United States Patent
Oren

(10) Patent No.: US 12,011,231 B2
(45) Date of Patent: Jun. 18, 2024

(54) METHOD FOR CORRECTING ELECTRODE POSITIONS OF AN ELONGATED MEDICAL DEVICE

(71) Applicant: ST JUDE MEDICAL INTERNATIONAL HOLDING S.À.R.L., Luxembourg (LU)

(72) Inventor: Eitan Oren, Haifa (IL)

(73) Assignee: ST JUDE MEDICAL INTERNATIONAL HOLDING S.À R.L., Luxembourg (LU)

(*) Notice: Subject to any disclaimer, the term of this patent is extended or adjusted under 35 U.S.C. 154(b) by 315 days.

(21) Appl. No.: 17/435,633

(22) PCT Filed: Mar. 4, 2020

(86) PCT No.: PCT/US2020/021026
§ 371 (c)(1),
(2) Date: Sep. 1, 2021

(87) PCT Pub. No.: WO2020/181006
PCT Pub. Date: Sep. 10, 2020

(65) Prior Publication Data
US 2022/0142713 A1 May 12, 2022

Related U.S. Application Data

(60) Provisional application No. 62/813,996, filed on Mar. 5, 2019.

(51) Int. Cl.
*A61B 34/20* (2016.01)
*A61B 5/00* (2006.01)
*A61B 5/06* (2006.01)

(52) U.S. Cl.
CPC .............. *A61B 34/20* (2016.02); *A61B 5/062* (2013.01); *A61B 5/6852* (2013.01); *A61B 2034/2072* (2016.02)

(58) Field of Classification Search
CPC . A61B 5/6852; A61B 2090/065; A61B 5/062; A61B 2017/00053; A61B 5/05; A61B 2034/2072
See application file for complete search history.

(56) References Cited

U.S. PATENT DOCUMENTS

2013/0066193 A1 3/2013 Olson et al.
2016/0367168 A1 12/2016 Malinin et al.
(Continued)

FOREIGN PATENT DOCUMENTS

CN 103813748 A 5/2014
CN 107771055 A 3/2018
(Continued)

OTHER PUBLICATIONS

Kabra, et al., "Recent Trends in Imaging for Atrial Fibrillation Ablation", Indian Pacing and Electrophysiology Journal,XP055048854, ISSN: 0972-6292, 11 CART0-3 11, May 5, 2010, pp. 215-227.
PCT/US20/21026, "International Search Report and Written Opinion", dated Aug. 17, 2020, 20 pages.
"Communication Pursuant to Article 94(3) EPC received for European Patent Application No. 20716620.8, dated Oct. 20, 2022", 5 pages.
"Notice of Reasons for Rejection dated Oct. 18, 2022", 5 Pages.
"Notice of Allowance Received dated Jun. 6, 2023", 2 Pages.
"Non-Final Office Action Mailed on Feb. 2, 2024", 12 Pages.

*Primary Examiner* — Gerald Johnson
(74) *Attorney, Agent, or Firm* — Billion & Armitage

(57) ABSTRACT

The present disclosure is directed to systems and methods that account for measurement errors acquired from electrodes of a medical device prior to generating an image of the medical device. A correction model is initially generated utilizing a specialized testing catheter that incorporates both electrodes and magnetic sensors. The testing catheter is identically configured to a clinical catheter that has no or fewer magnetic sensors. The testing catheter is used to collect responses (e.g., positions) from the magnetic sensors and electrodes. Electrode positions calculated from the more accurate magnetic sensors are mapped to potentially distorted positions determined from the electrode responses. The correction model (e.g., machine-learning algorithm) is trained using such relationships. Once trained, the correction (Continued)

model is implemented to adjust raw electrode responses prior to generating an image of a medical device. The correction model may adjust raw electrode responses of a clinical usage catheter that lacks magnetic sensors.

16 Claims, 12 Drawing Sheets

(56) References Cited

U.S. PATENT DOCUMENTS

| | | | |
|---|---|---|---|
| 2017/0105680 A1* | 4/2017 | Shushan | A61B 5/7221 |
| 2018/0296113 A1 | 10/2018 | Stewart et al. | |
| 2021/0068694 A1* | 3/2021 | Chou | A61B 5/027 |

FOREIGN PATENT DOCUMENTS

| | | |
|---|---|---|
| EP | 3138486 A1 | 3/2017 |
| JP | 2010131385 A | 6/2010 |
| JP | 2014511737 A | 5/2014 |
| JP | 2014530030 A | 11/2014 |
| JP | 2018519046 A | 7/2018 |

\* cited by examiner

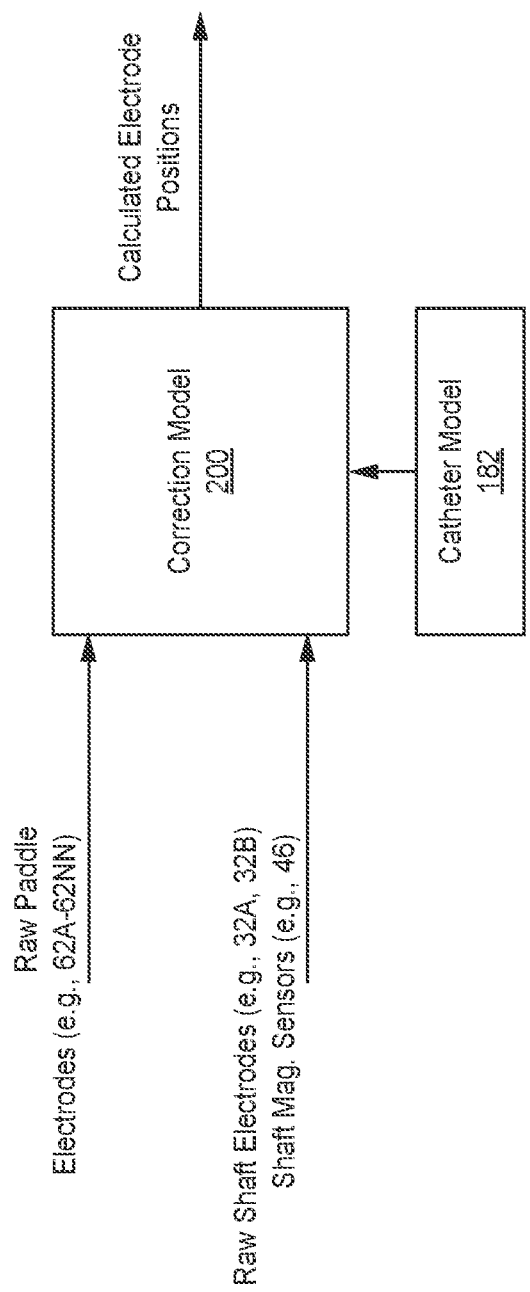

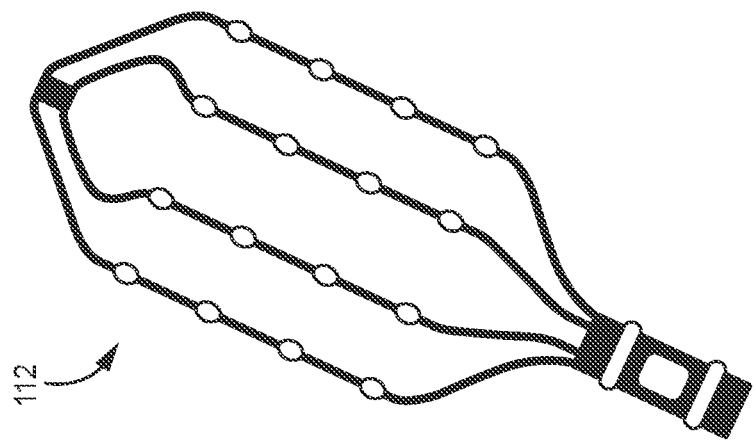
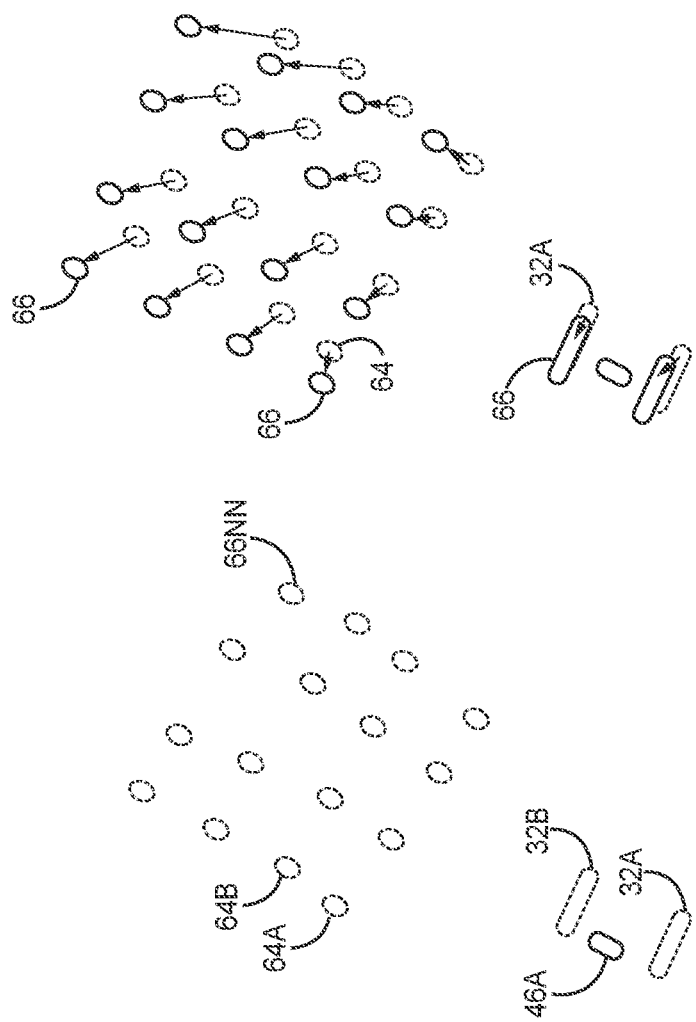
FIG. 12C
FIG. 12B
FIG. 12A

METHOD FOR CORRECTING ELECTRODE POSITIONS OF AN ELONGATED MEDICAL DEVICE

CROSS-REFERENCE TO RELATED APPLICATION(S)

This application is a National Stage Application of PCT/US20/21026, filed on Mar. 4, 2020, which claims benefit of U.S. provisional application 62/813,996, titled "A METHOD FOR CORRECTING ELECTRODE POSITIONS OF AN ELONGATED MEDICAL DEVICE", filed Mar. 5, 2019, and which applications are incorporated herein by reference. A claim of priority to all, to the extent appropriate, is made.

FIELD

The present disclosure relates generally to systems and methods for generating images of an elongated medical device based on position information obtained from sensors on the elongated medical device. More particularly, this disclosure relates to systems and methods for correcting electrode positions of an elongated medical device to prior to using the electrode positions to generate the images of the elongated medical device.

BACKGROUND

Catheters are used to perform a variety of tasks within human bodies and other bodies including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface, among other tasks. In order to properly administer treatment, the position and orientation of a catheter inside the body must be continuously monitored. One known technique for determining the position and orientation of a catheter within a body is by tracking a plurality of sensors on the catheter using a position sensing and navigation system (sometimes called a location mapping system). In one exemplary system offered for sale by St. Jude Medical, Inc., under the trademark "ENSITE NAVX", the sensors comprise electrodes. Excitation of pairs of electrodes on the outer surface of the body generates electrical fields within the body. Voltage measurements on the catheter electrodes can then be used to determine the position and orientation of the catheter electrodes within a coordinate system of the position sensing and navigation system. Other exemplary position sensing and navigation systems include magnetic systems.

In order to provide information to clinicians about the position and orientation of the catheter, the determined position and orientation of the catheter sensors is often used to render an image of the catheter relative to surrounding tissues, including heart tissues. One drawback to conventional systems, however, is that the determined position and orientation of the catheter sensors is subject to systematic errors due to subtle differences in, e.g., sensor impedances and amplifier channels. That is, electric-field based navigation systems are subject to various types of interference that can impact the accuracy of position measurements. For example, the level of electrical impedance in the patient body is not necessarily constant. The impedance can slowly drift or even undergo transient shifts due to, for example, a change in medication leading to drift and/or shift in the detected position of the medical device. Various methods have been proposed to mitigate potential drift or shift including bio-impedance scaling, patch center subtraction and the use of a fixed reference catheter with a reference electrode. Bio-impedance scaling and patch center subtraction help to reduce drift and shift, but do not eliminate all cases of drift and shift. The use of a fixed reference catheter requires insertion of an additional catheter into the body thereby increasing procedure time and the risk of complications. Further, the reference catheter may become dislodged during the procedure. As a result, geometries and representations (e.g., images) that are rendered based on position measurements may appear distorted. That is, various errors can distort the rendered shape of the catheter from its true mechanical shape (e.g., within a body of a patient) in the resulting image.

There is thus an ongoing a need for a system and method for navigating a medical device within a body that will minimize and/or eliminate one or more of the above-identified deficiencies.

BRIEF SUMMARY OF THE DISCLOSURE

Various embodiments herein provide systems, methods and/or non-transitory computer readable medium storing instructions (i.e., utilities) for use in correcting electrode positions of a medical device (e.g., catheter) configured for disposition within a patient body prior to using those electrode positions to generate a shape and corresponding image of the medical device. In an arrangement, a correction model is generated utilizing a specialized testing catheter that incorporates both electrodes and magnetic sensors. The testing catheter is identically configured to a clinical usage catheter that has no or fewer magnetic sensors. The testing catheter is used to collect responses (e.g., positions) from the magnetic sensors and electrodes. Electrode positions calculated from the more accurate magnetic sensors are mapped to potentially distorted electrode positions determined from the electrode responses. The correction model (e.g., machine-learning algorithm) is trained using such relationships. Once trained, the correction model is implemented to adjust raw electrode responses prior to generating a shape and/or image of a medical device. The correction model may adjust raw electrode responses of a clinical usage catheter that lacks magnetic sensors.

In an embodiment, utilities are directed to correcting electrode positions of a medical device such as a catheter configured for disposition within a patient body. Initially, the utilities acquire a plurality of data sets from a first catheter (e.g., testing catheter) having a plurality of electrodes and a plurality of magnetic sensors. Each data set includes information related to measured positions of the electrodes and measured positions of the magnetic sensors. The utilities map the measured position of each electrode, which may include distortion, to a calculated electrode position that is determined, at least in part, from the measured position of the magnetic sensors. Typically, the calculated electrode positions will have a higher accuracy than the measured positions. The mapping defines a correction model that maps measured electrode positions to calculate electrode positions. Once the correction model is generated, a subsequent set of measured electrode positions is acquired. In an arrangement the subsequent set of measured electrode positions is acquired from a second catheter (e.g., clinical usage catheter) having identical configuration to the first catheter. However, the second catheter may lack the magnetic sensors of the first catheter. However, the first and second catheters have a common shape (e.g., an undeflected state) and electrode configuration. The subsequent set of measured electrode positions, which may include distortion, are input into the correction model, which generates a set of calculated electrode positions based on the prior known relationships obtained from the first catheter. The set of calculated electrode positions are then utilized to generated catheter shape of the second catheter which may be output as an image to a display.

In an arrangement, the mapping entails training a machine-learning algorithm to identify the relationships between the magnetic sensor positions and the electrode positions acquired from the first catheter (e.g., testing catheter). In such an arrangement, the magnetic sensor positions may be utilized with a catheter model corresponding to the testing catheter (and the clinical usage catheter) to generate a shape of the testing catheter for a given set of magnetic responses. This catheter shape may then be utilized to determine the calculated electrode positions based on known spacings between the magnetic sensors and the electrodes of the testing catheter. In such an arrangement, offsets between the measured electrode responses and the calculated electrode responses may be identified and utilized to train the machine learning algorithm. The mapping may entail acquiring data sets for hundreds, thousands or even millions of positions and orientations of the testing catheter while disposed within a three-dimensional space.

In another embodiment, utilities are provided for training and using a machine-learning algorithm to correct electrode positions. In one arrangement, the utilities initially train a machine learning algorithm using a plurality of measured electrode positions and measured magnetic sensor positions acquired from a testing catheter, which includes both electrodes and magnetic sensors. The machine-learning algorithm is configured to identify relationships between measured electrode positions and calculated electrode positions, which are determined from the measured magnetic sensor positions. In an arrangement, the initial training utilizes data acquired in the lab where the differences between measured electrode positions and actual electrode positions is known. Once initially trained, the machine learning algorithm may be further refined (e.g., trained) during catheter usage (e.g., animal testing). In such an arrangement, the testing catheter acquires subsequent electrode responses and magnetic responses. The electrode responses are input into the machine learning algorithm which generates a set of calculated electrode positions. These calculated electrode positions are utilized, in conjunction with a catheter model, to generate a catheter shape. Predicted magnetic sensor positions are determined from the catheter shape based on known spatial relationships between the electrodes and magnetic sensors of the testing catheter. The difference between the predicted magnetic sensor positions and the subsequently measured magnetic sensor positions are utilized to calculate an error value for the machine-learning algorithm. This error value may be utilized to refine the machine-learning algorithm.

In an arrangement, the process after initial training is repeated for a multitude of catheter positions and orientations and until a calculated error value is below a predetermined threshold. At this time, the machine learning algorithm is trained for clinical usage and defines a correction model. The correction model may be utilized with a clinical usage catheter that is identically configured to the testing catheter, with the exception of a corresponding number of magnetic sensors. The clinical usage catheter may have fewer magnetic sensors than the testing catheter or entirely lack magnetic sensors. The clinical usage catheter may be utilized in a clinical procedure (e.g., with a patient) to obtain electrode positions/responses. These electrode positions/responses may be input to the correction model, which generates a set of corrected electrode positions. The correct electrode positions may be utilized to generate a shape of the catheter, which may be output as an image to a display.

In another embodiment, utilities are provided that use a correction model to adjust electrode positions acquired from a clinical usage catheter. In an arrangement, a clinical usage catheter is inserted into a patient body. A medical positioning system may acquire electrode responses from electrodes of the clinical usage catheter. These electrode responses may be input into a trained machine-learning algorithm that maps measured electrode responses to calculated electrode responses. In such an arrangement, the machine learning algorithm may be trained on training data obtained from a testing catheter that has identical shape (e.g., when undeflected) as the clinical usage catheter and an identical electrode configuration. The testing catheter may further include a plurality of magnetic sensors. The machine learning algorithm utilizes data from the electrodes and magnetic sensors of the testing catheter to determine relationships between measured electrode positions and electrode positions calculated from the magnetic sensors. The machine learning algorithm outputs calculated electrode positions for the input responses obtained from the clinical usage catheter. These calculated electrode positions may adjust for distortions in the measured responses and may be utilized to generate a shape and corresponding image of the catheter which may be output to display.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 11 illustrates use of a correction model to output calculated electrode positions, FIGS. 12A-12C illustrate the process of FIG. 11.

DETAILED DESCRIPTION

Referring now to the figures, in which like numerals indicate the same or similar elements in the various views, The disclosure provides systems and methods for use in generating an image of an elongate medical device (e.g., a catheter) within a body. In particular, the systems and methods described herein are suitable for generating images of various elongate medical devices by measuring positions of electrodes on the elongate medical device.

More specifically, the methods and systems described herein allows for generating an image of an elongate medical device (e.g., as disposed within a body of a patient) while accounting for various distortions in the measured responses (e.g., positions or locations) of the electrodes. The disclosed methods and systems apply a correction to a set of raw electrode responses (e.g., which may include distortions) to generate adjusted responses. Once the raw responses are corrected, the corrected responses more accurately represent the actual locations of the electrodes of the medical device within the body of a patient. Such a correction is applied prior to generation of the image thereby improving the accuracy of the generated image. In an embodiment, the correction is generated based on the comparison of a set of current raw electrode responses to predetermined sets of raw electrode responses (e.g., measurements) mapped to actual electrode responses that are based on estimated electrode positions determined from magnetic sensors. In an embodiment the correction is based on raw electrode responses for electrodes of a medical device that are acquired in conjunction with a set of magnetic responses for magnetic sensors of that medical device. Such magnetic responses typically have a greater accuracy than the electrode responses. Utilizing known relative orientations between the electrodes and the magnetic sensors as disposed on the medical device, the calculated or actual positions/responses of the electrodes may be determined based on the magnetic responses. In an embodiment, a machine learning algorithm may be trained using multiple (e.g., hundreds, thousands or millions) of sets of electrode and magnetic responses for a given catheter configuration to generate a correction model (e.g., for a given catheter configuration), which predicts the actual locations of a set of electrodes based on raw responses of the electrodes. Once the correction model is established (e.g., trained), the correction model may be used to predict the actual responses of the electrodes in the absence of magnetic sensors.

Figure 1:
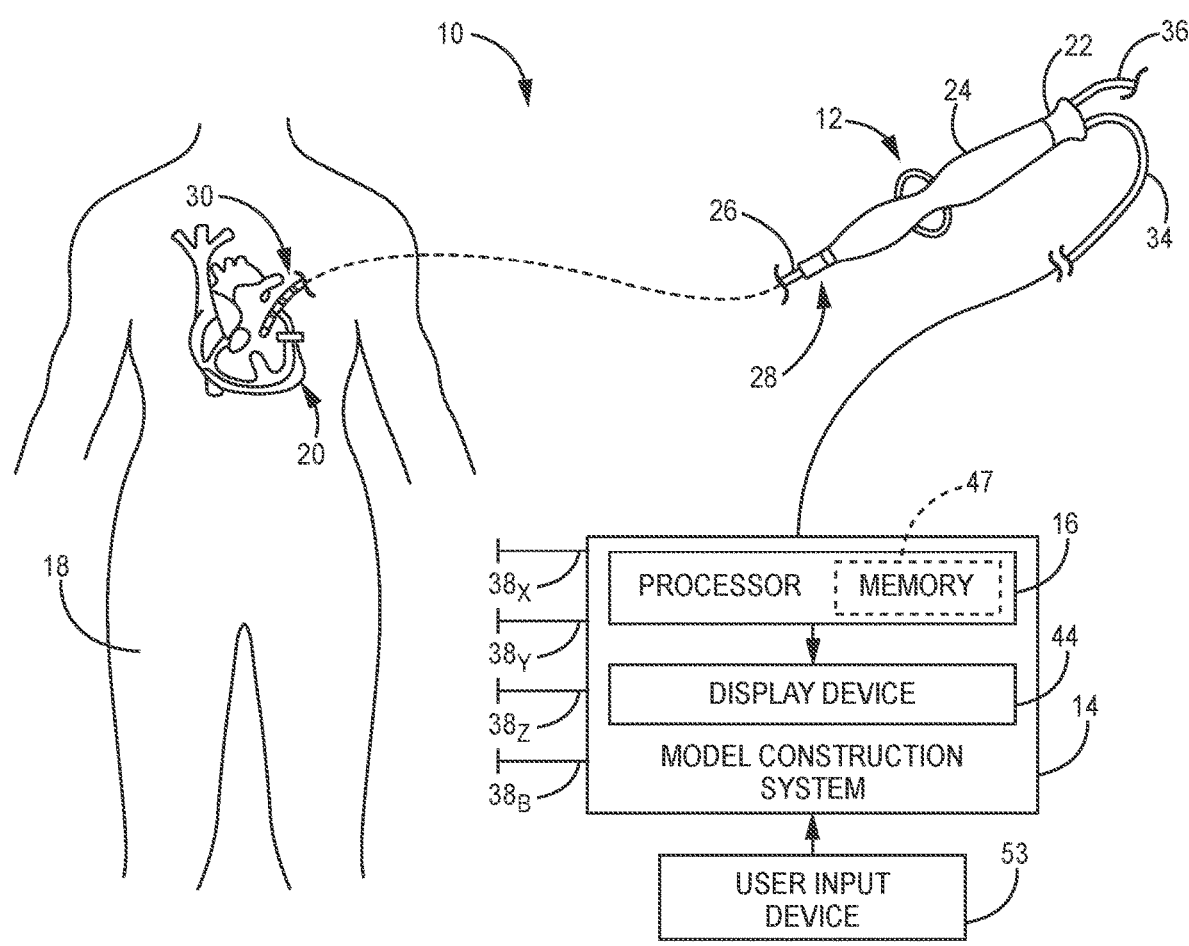
FIG. 1 is a diagrammatic view of a system for generating images of a medical device.

Referring now to the drawings wherein like reference numerals are used to identify identical components in the various views, FIG. 1 illustrates one exemplary embodiment of a system 10 for generating an image of an elongated medical device within a body of a patient. In this embodiment, the system 10 includes, among other components, an elongate medical device and a model construction system 14. In this embodiment, the elongated medical device is a catheter 12 and the model construction system 14 includes, among other components, a processing apparatus 16. The processing apparatus 16 may take the form of an Electronic Control Unit (ECU), for example, that is configured to generate and render an image of catheter 12 and output the image of the catheter to a display 44. Although the system is described in terms of rendering a catheter, it should be understood that various elongate medical devices (e.g., introducer sheaths, pacing leads, etc.) could be rendered using the system. Further, the processing apparatus 16 may be utilized, at least in part, to generate the correction model/machine learning algorithm as discussed herein.

As illustrated in FIG. 1, the catheter 12 is configured to be inserted into a patient's body 18, and more particularly, into the patient's heart 20. The catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient). The catheter 12 may comprise an electrophysiological (EP) catheter for use in gathering EP data associated with the heart 20 to enable generation of an image of the geometry of the heart surface and related EP data. The catheter 12 may also allow removal of bodily fluids or injection of fluids and medicine into the body and may further provide a means for transporting surgical tools or instruments within a body including those used for pacing or tissue ablation. Although the catheter 12 is described as an EP catheter in the illustrated embodiment, it should be understood that the system can be used to visually render a variety of different types of catheters including, for example, intracardiac echocardiography (ICE) catheters and ablation catheters using a wide variety of ablative energies (e.g., radio-frequency, cryogenic, ultrasound, laser or other light, etc.).

Figure 2:
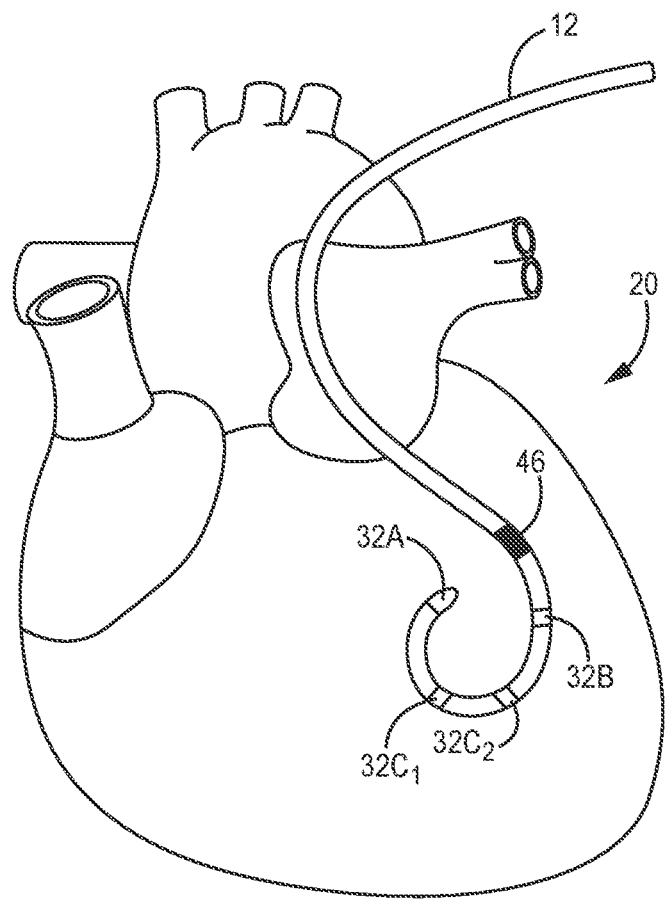
FIG. 2 is a diagrammatic view of a distal end of a catheter used in the system shown in FIG. 1 within a human heart.

Referring to FIG. 2, the catheter 12 may include a plurality of EP mapping electrodes 32 such as distal tip electrode 32A, proximal ring electrode 32B, and intermediate ring electrodes $32C_1$ and $32C_2$. The electrodes 32 are provided to generate information regarding the position of catheter 12 and therefore may function as position sensors in accordance with the present disclosure. The electrodes 32 may also provide information regarding the geometry of the heart 20. The catheter 12 may also include one or more magnetic position sensor(s) 46. The magnetic position sensor(s) 46 are also provided for use in determining the position of the catheter 12 within a body. In the illustrated embodiment, the magnetic sensor 46 is disposed within the shaft of the catheter and is formed of a coil. However, it should be understood that the magnetic sensor(s) 46 may take other forms. That is the magnetic sensor(s) may, for example, comprise any conventional position sensors for detecting changes in magnetic fields including Hall effect sensors, magnetoresistive sensors and sensors made from magnetoresistive materials and piezoelectric materials and the like. If present, the magnetic position sensor(s) 46 provide information regarding the position of the catheter and therefore may function as position sensors in accordance with the present disclosure. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The connector 22 provides mechanical, fluid, and electrical connection(s) for cables, such as, for example, cables 34, 36 extending to model construction system 14 and/or other components of system 10 (e.g., a visualization, navigation, and/or mapping system (if separate and distinct from model construction system 14), an ablation generator, irrigation source, etc.). The handle 24, which is disposed at the proximal end 28 of the shaft 26, provides a location for the clinician to hold the catheter 12 and may further provide means for steering or guiding the shaft 26 within the body 18 of the patient. For example, the handle 24 may include means to change the length of a steering wire extending through the catheter 12 to its distal end 30 to steer the shaft 26. In other embodiments, the catheter 12 may be robotically driven or controlled. The shaft 26 is an elongated, tubular, flexible member configured for movement within the body 18 and supports, for example and without limitation, sensors and/or electrodes mounted thereon, such as, for example, sensors 32, associated conductors, and possibly additional electronics used for signal processing and conditioning. The shaft 26 may also permit transport, delivery, and/or removal of fluids (including irrigation fluids, cryogenic ablation fluids, and bodily fluids), medicines, and/or surgical tools or instruments. The shaft 26 may be introduced into a blood vessel or other structure within the body 18 through a conventional introducer and may then be steered or guided through body 18 to a desired location, such as heart 20, using means well known in the art.

Figure 3:
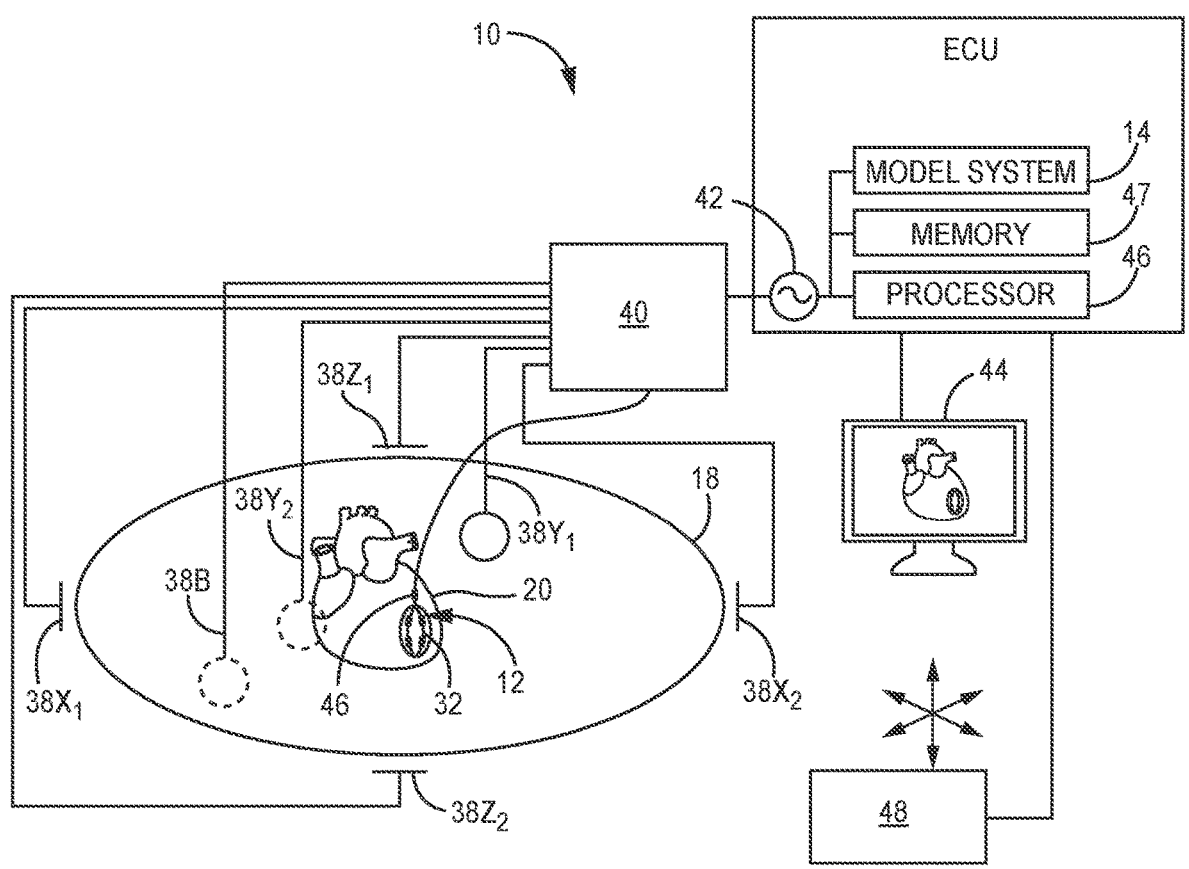
FIG. 3 is a diagrammatic view of a system configured to measure electrode response and magnetic responses from medical devices disposed within a body of a patient.

With reference to FIG. 3, in addition to the processing apparatus 16 and the model construction system 14, the system 10 may include, among other possible components, a plurality of patch electrodes 38, a multiplex switch 40, a signal generator 42, and a display device 44. In other embodiments, some or all of these components are separate and distinct from model construction system 14 but are electrically connected to, and configured for communication with the model construction system 14.

The processing apparatus 16 may include a programmable microprocessor or microcontroller, or may include an application specific integrated circuit (ASIC). Further, the processing apparatus 16 may include a central processing unit (CPU) and an input/output (I/O) interface through which the processing apparatus 16 may receive a plurality of input signals including, for example, signals generated by patch the electrodes 38 and the position sensors 32. Further the processing apparatus may generate a plurality of output signals including, for example, those used to control and/or provide data to, for example, display device 44 and switch 40. Processing apparatus 16 may be configured to perform various functions, such as those described in greater detail above and below, with appropriate programming instructions or code (i.e., software). Accordingly, the processing apparatus 16 is programmed with one or more computer programs encoded on a computer storage medium for performing the functionality described herein.

With the possible exception of patch electrode $38_B$ called a "belly patch electrode," the patch electrodes 38 are provided to generate electrical signals used, for example, in determining the position and orientation of the catheter 12 within a three-dimensional coordinate system and in generating EP data regarding the heart 20. In one embodiment, patch electrodes 38 are placed orthogonally on the surface of the body 18 and are used to create axes-specific electric fields within body 18. For instance, in one embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. In addition, a reference electrode (not shown) may also be attached to body 18. Each of patch electrodes 38 may be coupled to multiplex switch 40. In this embodiment, the processing apparatus 16 is configured, through appropriate software, to provide control signals to the switch 40 to thereby sequentially couple pairs of electrodes 38 to the signal generator 42. Excitation of each pair of electrodes 38 generates an electric field within the body 18 and within an area of interest such as the heart 20. Voltage levels at non-excited electrodes 38, which are referenced to the belly patch electrode $38_B$, are filtered and converted and provided to the processing apparatus 16 for use as reference values.

Electrodes 32 on the catheter 12 are disposed within electrical fields created in body 18 (e.g., within the heart 20) by exciting the patch electrodes 38. These electrodes 32 experience voltages that are dependent on the location between the patch electrodes 38 and the position of the electrodes 32 relative to the surface of the heart 20. Voltage measurement comparisons (e.g., impedance responses) made between the electrodes 32 can be used to determine the position of the electrodes 32 within the heart 20. Movement of the electrodes 32 within the heart 20 (e.g., within a heart chamber) produces information regarding the geometry of the heart 20 as well as EP data. Though discussed with respect to an orthogonal arrangement of patch electrodes 38, the present disclosure is not meant to be so limited. Rather, in other embodiments, non-orthogonal arrangements (e.g., arrangements of non-orthogonal dipoles) may be utilized to determine the location coordinates (e.g., positions) of the electrodes 32.

The system 10 is provided to determine the position and orientation of position sensors such as the electrodes 32 on an elongate medical device such as the catheter 12. The model construction system 14 uses this position and orientation data to generate an image of the catheter 12 within the heart 20. More particularly, the processing apparatus 16 of the model construction system 14 is configured to acquire measured data points (e.g., impedance responses) collected using the position sensors 32 (i.e., electrodes 32), where the measured data points corresponding to respective positions of electrodes 32. In this embodiment, the model construction system 14 acquires the measured data points by activating electrodes 32 as described above. In other embodiments, however, the model construction system 14 may simply acquire the measured data points from the electrodes 32 or another component in the system 10, such as, for example, a memory or other storage device that is part of the model construction system 14 or accessible thereby, without affirmatively taking part in the collection of the measured data points. Generally, the model construction system 14 is configured to describe the measured data points as deviations from a parametric form (e.g., a curve, in the case of a one-dimensional catheter 12, or a plane, in the case of a two-dimensional catheter 12) and generate an image of the catheter using such deviations. Stated otherwise, the model construction system utilizes the measured data points with a mathematical model that describes a particular catheter supporting the electrodes to generate an image of that catheter based on the positions of the data points.

As further shown in FIG. 3, the system 10 may further incorporate a magnetic field-based system to determine the position and orientation of a catheter and/or similar medical devices within a body. In such a system, a magnetic field generator 48 may be employed having three orthogonally arranged coils, arranged to create a magnetic field within the body and to control the strength, orientation, and frequency of the field. The magnetic field generator 48 may be located above or below the patient (e.g., under a patient table) or in another appropriate location. Magnetic fields are generated by coils of the magnetic field generator and current or voltage measurements for one or more magnetic position sensors 46 (e.g., magnetic field sensors) associated with the catheter 12 are obtained. The measured currents or voltages are proportional to the distance of the sensors from the coils thereby allowing a position of the sensors within a coordinate system of the system. The positions of the sensors may be utilized to generate an image of the medical device on a display relative to, for example only, a cardiac model or geometry. Exemplary embodiments of magnetic field-based medical positioning systems are set forth in co-owned U.S. Pat. No. 7,386,339 and U.S. Pat. App. No 2013/0066193, hereby incorporated by reference in their entirety.

When utilizing a dual electric field-based system (e.g., impedance-based system) and magnetic field-based system, the system 10 may utilize, for example, the EnSite™ Velocity™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, the system 10 may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

In summary, the electrodes 32 and/or magnetic sensors 46 of the catheter 12 are electrically coupled to the processing apparatus 16 and are configured to serve a position sensing function. In the case of the electrodes, the electrodes 32 are placed within electric fields created in the body 18 (e.g., within the heart) by exciting the patch electrodes 38. Using various known algorithms, the processing apparatus 16 may then determine the location (position and orientation) of each electrode 32 and record it as a measured data point corresponding to a respective position of each electrode 32 in a memory or storage device, such as a memory 47, associated with or accessible by the processing apparatus 16. These data points may then be utilized by the model construction system to generate an image of the catheter.

The electric field-based system provides the ability to simultaneously locate a relatively large number of electrodes and has found widespread acceptance and use in the industry. However, because electric field-based systems employ electrical current flow in the human body, these system can be subject to measurement inaccuracies due to shift and/or drift caused by various physiological phenomena (e.g., local conductivity changes, sweat/patch interactions, etc.). Additionally, electric field-based system may be subject to electrical interference. As a result, electrode locations, renderings, geometries and/or representations based on the raw responses of electrodes of such electric field-based system may be distorted. Accordingly, it is desirable to adjust the raw responses to account for such distortions.

Efforts have been made to account for such distortions or errors associated with electric field-based system by combining an electric field-based system with a magnetic-field based system, which is independent from patient anatomy and generally provides higher accuracy in comparison with an electric field-based system. Magnetic field-based systems determine magnetic position sensor locations (e.g., position and orientation) in a magnetic coordinate system based on capturing and processing signals received from a magnetic position sensor while the sensor is disposed in a controlled low-strength alternating current (AC) magnetic (e.g., magnetic) field. Each magnetic position sensor typically comprises a coil. From an electromagnetic perspective, the changing or AC magnetic field induces a current in the coil(s) when the coil(s) are in the magnetic field. The magnetic position sensor is thus configured to detect one or more characteristics (e.g., flux) of the magnetic field(s) in which it is disposed and generate a signal indicative of those characteristics, which is further processed by a medical positioning system to obtain a respective P&O for the magnetic sensor(s) relative to, for example, a magnetic field generator.

In an embodiment, a combined medical positioning system combines an electric field-based system with a magnetic field-based system. In such an arrangement, locations of electrodes may be identified in an impedance-based coordinate system in conjunction with identifying the locations of one or more magnetic sensors in a magnetic-based coordinate system. In an embodiment, at least a portion of the electrodes and magnetic sensors may be co-located to define fiducial pairs. This co-location allows for determining a transformation (e.g., transformation matrix) between the coordinate systems. The transformation may be applied to the locations of any electrode to register these locations in the magnetic-based coordinate system once the transformation is determined. Accordingly, the electrical impedance-based electrodes can be identified in the coordinate system of the magnetic field-based positioning system thereby increasing the positioning accuracy for the electrodes. The combined system, while providing improved accuracy, has a number of shortcomings. For instance, due to the size of the magnetic sensors, it typically is not feasible to co-locate a magnetic sensor with each electrode. Therefore, most systems continue to utilize data points acquired from electrode to generate an image of a catheter or other medical device.

One system and method for utilizing the data points to generate an image of a catheter is set forth in U.S. Pat. Pub No. 2018/0014751 entitled "Methods and Systems for Generating Soothed Images of an Elongate Medical Device" the entire disclosure of which is incorporated herein by reference. Broadly, the described method and system described by 2018/0014751 smooths measured data points by applying an error term to the raw data points utilized to generate am image of the medical device. In a first step of a process for generating images as set forth by U.S. Pat. Pub No. 2018/0014751, measured data points corresponding to measured positions of each electrode on catheter are acquired. Electrode position measurements, are expressed as a true position plus measurement error:

$$X = \langle X \rangle + \in$$

where X represents the measured position of an electrode 32 on catheter 12 (e.g., see FIG. 2), $\langle X \rangle$ represents a true position of the electrode 32, and $\in$ represents measurement error in the measured position, or the deviation from an idealized or true parametric form.

Measured positions of other points on the same catheter 12, such as measured positions of other electrodes 32, are used to reduce the remaining error in measured electrode positions. Though the true position, orientation, and/or shape of catheter 12 on which electrodes 32 are disposed are not known, these may be inferred from a collection of the measured positions of electrodes 32 on catheter 12. Generally, a "parameterized catheter" may refer to a catheter 12 for which a set of parameters (e.g., position, orientation, shape, length, number of electrodes 32, distance between adjacent electrodes 32, etc.) determine the true position of an electrode 32. That is, a mathematical model defines the catheter and this mathematical model may be used to reduce the error in the measured electrode positions.

A coordinate system associated with catheter 12 (a "catheter coordinate system") is then established. The individual electrode measurement errors can then be described as deviations from the true positions, as determined by the parameterized catheter (e.g., catheter model) and an inferred estimate of the true parameters, assuming that the measurement errors for each electrode 32 are independent and normally distributed. In an embodiment, true parameters are estimated or inferred to be those parameters that minimize a sum of squared measurement errors between the parametrized position and the measured positions.

$$\langle X_i \langle =f(\rangle p \rangle, U_i \rangle$$

where $X_i$ represents the true position of electrode i, p represents a set of true parameters, and $U_i$ represents a coordinate in the catheter coordinate system for electrode i.

In a subsequent step, a coordinate $U_i$ for each electrode 32 is calculated. For curved or linear one-dimensional catheters 12, $U_i$ is a scalar representing an arclength between the distal-most electrode (e.g., electrode 32A) and electrode i along shaft 26 of catheter 12, and p is composed of a curve parameter and an affine transformation $\{\Theta, M\}$. The parametric form of catheter 12 can be then described which defines the possible domain in which true positions of electrodes 32 may lie. For curved or linear one-dimensional catheters, the true positions are described by a single curve of constant curvature, such that the true position of each electrode must fit a curve defined by curve parameter $\Theta$ and affine projection M. For an exemplary planar catheter 12' (see e.g., FIG. 4), $U_i$ is a two-dimensional coordinate in a plane defined by a surface of the catheter 12'. A first term $(U_{1,1})$ specifies a distance in the distal to proximal direction $U_i$ along central axis of catheter 12', and a second term $(U_{1,2})$ specifies a distance from central axis perpendicular to the central axis, for example, direction $U_2$. In addition, p is composed of a curvature term, a torsion term, and an affine transformation: $\{\kappa, \tau, M\}$. $\kappa$ and $\tau$ are constants over the plane defined by the surface of the catheter 12'. For two-dimensional catheters, the true positions are described by an exemplary two-dimensional parametric form including curvature ($\kappa$) and torsion ($\tau$) terms.

In a further step, an estimate of the true parameters is computed as a non-linear least-squares solution to the original measurements. Solvers such as Levenberg-Marquardt may be used for this purpose. For all parameterized models, the measurement error $\in$ is described by a thin-plate spline in the dimensionality of $U_i$, with a per-electrode stiffness specified by $\lambda_i$. "Stiffness" may be further described as a parameter that defines how much variation in the measured position of each electrode 32 is permitted. A measurement error for each electrode 32 (i.e., the measurement error in the measured position of each electrode 32) is calculated, based at least in part on stiffness parameter $\lambda_i$. Smoothed data points are calculated and used to generate an image and display the image.

While providing a means for accounting for measurement errors, this previous system and method provides no adjustment to the measured responses (e.g., data points) prior to utilizing the data points to generate an image. That is, the measured positions are defined as a true position plus a measurement error. The presented systems and methods provide a correction to the measured positions prior to their use in generating an image. That is, the measured positions are adjusted/corrected prior to their subsequent use in generating an image. Along these lines, the present system may be utilized to adjust the measured positions prior to their use in a model construction system such as that set forth in U.S. Pat. Pub No. 2018/0014751 further improving the overall accuracy of a generated image.

The present disclosure is based in part on the realization that it is possible to utilize the greater accuracy of a magnetic field-based system with an electric field-based system for catheters and other medical devices that may have no or few magnetic sensors. Specifically, it has been determined that a correction model may be generated utilizing a specialized testing or mapping device (e.g., testing catheter or mapping catheter) that incorporates both electrodes and magnetic sensors. The mapping catheter may be identically configured to a clinical usage catheter (e.g., standard catheter) that has no or fewer magnetic sensors. In such an embodiment, the electrodes of the mapping catheter and the electrodes of the clinical usage catheter are arranged in a common configuration or layout (e.g., number and spacings). The mapping catheter may be utilized to collect responses from the magnetic sensors and electrodes such that positions and orientations associated with the more accurate magnetic sensors (e.g., actual electrode positions estimated or calculated based on the measured magnetic sensor positions) may be mapped to the potentially distorted positions and orientations of the electrodes. That is, relationships of the magnetic sensors and electrodes may be identified. A correction model may be trained using such relationships. Once trained, the correction model may be used to adjust a set of electrode responses based on prior known relationships between electrode responses (e.g., positions) and magnetic sensor responses (e.g., positions) to improve the accuracy of the electrode responses prior to generating an image of a medical device. Further, such a correction model may be applied to raw electrode responses of a medical device (e.g., clinical usage catheter) even if that device lacks magnetic sensors.

Figure 4A:
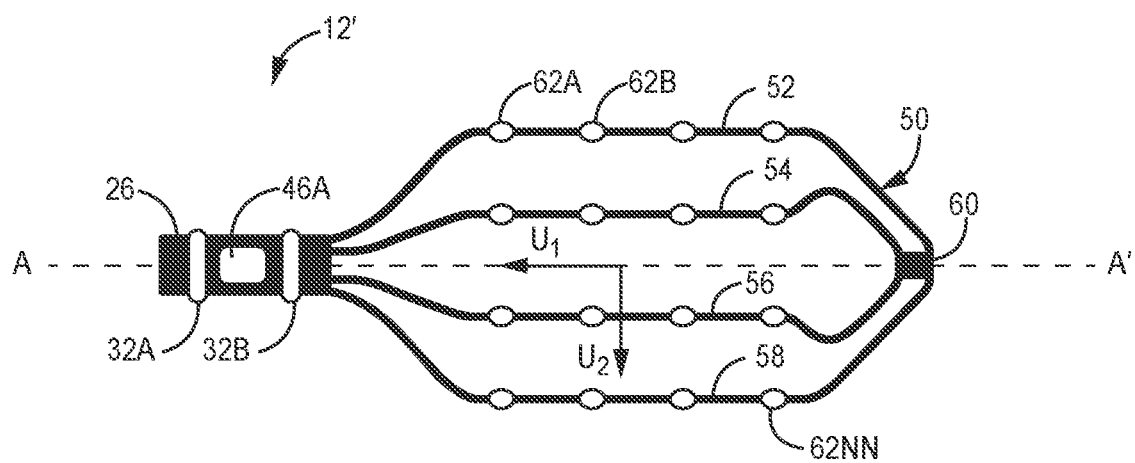
FIGS. 4A and 4B are exemplary embodiments of a testing/mapping catheter and a usage catheter.
Figure 4B:
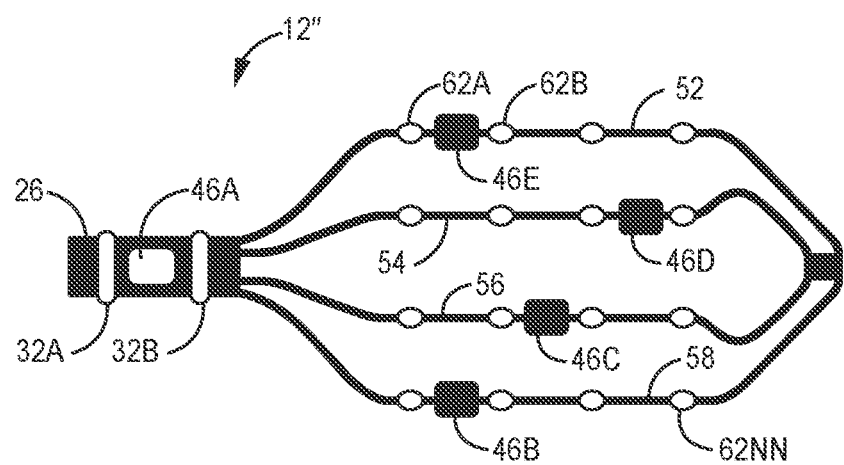

FIGS. 4A and 4B illustrates one embodiment of a planar catheter 12' (e.g., clinical usage catheter or standard catheter) and a correspondingly configured mapping catheter 12" (e.g., testing catheter). These corresponding catheters and their corresponding configuration are discussed throughout the remainder of the description. However, it will be appreciated that the presented systems and methods are not limited to any particular catheter configuration and the systems and methods described herein may be applied to other catheters (e.g., single spline, basket type catheters, etc.). As shown in FIG. 4A, the clinical usage catheter 12' comprises a catheter shaft 26 coupled to a paddle 50. In the illustrated embodiment, the catheter shaft 26 includes a first shaft electrode 32A and a second shaft electrode 32B. Disposed between the shaft electrodes is a magnetic sensor/coil 46A. As illustrated, the paddle 50 includes four splines 52, 54, 56, and 58 that are coupled to the catheter shaft 26 by a proximal coupler (not shown) and which are coupled to each other by a distal connector 60 at a distal end of the paddle 50. In one embodiment, the first and fourth spline 52, 58 can be one continuous segment, and the second and third splines 54, 56 can be another continuous segment. In other embodiments the various splines can be separate segments coupled to each other. The plurality of splines can further comprise a varying number of electrodes 62A-62NN (hereafter 62 unless specifically referenced). The electrodes 62 in the illustrated embodiment comprise sixteen ring electrodes (e.g., four electrodes per spline) evenly spaced along the splines. In other embodiments the electrodes 62 can be evenly or unevenly spaced and the electrodes can comprise point or other types of electrodes.

The splines 52-58 generally line in a common plane when the paddle 50 of the clinical usage catheter 12' is in an undeflected state. This plane defines a surface of the paddle 50 and includes a central axis A-A' aligned with the shaft 26 when the paddle is undeflected. Although the paddle 50 is illustrated as flat or planar in FIG. 4A, it should be understood that the paddle 50 may bend, curl, buckle, twist, and/or otherwise deform. Accordingly, the plane defined by the paddle 50 may correspondingly deform, such that the plane is a non-flat topological plane. The positions each electrodes 62A-NN may be described using a distance along a direction $U_i$ a distal-to-proximal direction along central axis A-A', and a direction $U_2$, a direction from the first spline 52 towards the fourth spline 58. Further, curvature and/or torsion parameters may be defined for each electrode to define the location of the electrode in three dimensions.

FIG. 4B illustrates a 'mapping catheter' 12" (e.g., testing catheter) that is substantially identical to the clinical usage catheter 12' of FIG. 4A with the exception that the mapping catheter 12" includes a plurality of magnetic sensors 46B-46E (not necessarily to scale) disposed on the splines 52-58 in addition to the electrodes 62A-NN. The mapping catheter 12" is otherwise identically configured to the clinical usage catheter 12' and utilizes like figures for like components. Due to its common construction, the mapping catheter 12" bends, curls, buckles, twists, and/or otherwise deforms in a manner that is substantially identical to that of the planar catheter 12'. In the illustrated embodiment, the spline magnetic sensors 46B-46E are positioned at different locations along the length of the individual splines 52-58. Such differing spacing of the magnetic sensors allows for better determining the shape of the mapping catheter. The electrodes of the mapping catheter 12" are arranged in a common configuration (e.g., number and spacings) with the electrodes of the clinical usage catheter 12'.

As previously noted, the magnetic sensors are not subject to the various distortions and/or errors that affect the electrodes. Along these lines, measured positions of the magnetic sensors have a higher accuracy than the measured positions (e.g., responses) of the electrodes. However, due to the typically larger size of the magnetic sensors 46 in comparison to the electrodes 32, it may not be feasible to incorporate a full set of magnetic sensors into a clinical usage catheter that will be used in medical applications. However, it has been recognized that a mapping/testing catheter that utilizes both electrodes and magnetic sensors may be implemented in lab and animal testing to collect data for use in modeling the distorted responses/positions of the electrodes to the more accurate positions as determined by the relationship of the electrodes to magnetic sensors.

Figure 5A:
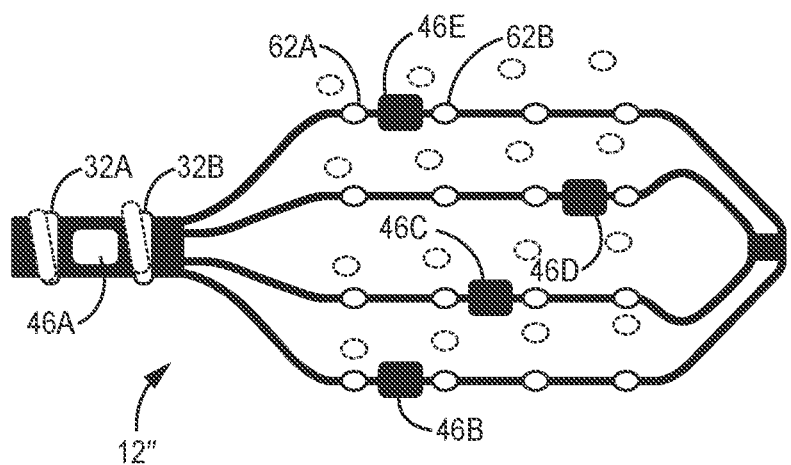
FIG. 5A illustrates distortion of measured electrode positions relative to actual electrode positions.
Figure 5B:
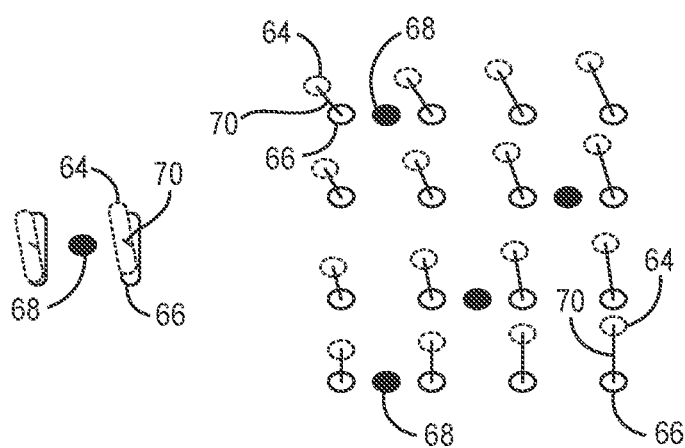
FIG. 5B illustrates deviation between measured electrode positions and actual electrode positions.

FIGS. 5A and 5B illustrate the use of the mapping catheter 12" to acquire data sets or data points (e.g., responses/positions) from both the electrodes 32A, 32B and 62A-NN and the magnetic sensors 46A-46E. Initially, the mapping catheter 12" may be disposed within a three-dimensional space (e.g., animal body) and the electric field-based and magnetic field-based systems may be operated to acquire data points (e.g., positions) for the electrodes and magnetic sensors, respectively. As shown, due to various distortion associated with the electrodes as previously discussed, the electrode responses/positions 64, as represented by the dashed ovals, may be offset from their actual positions 66 (e.g., as estimated or otherwise calculated based on the positions of the magnetic sensors), as represented by the solid ovals in FIG. 5B. In contrast, the magnetic responses/positions 68 are expected to be located at or near the actual positions of their magnetic sensors 46 as shown in FIG. 5A. Based on the actual positions 68 of the magnetic sensors 46, the actual positions 66 of the electrodes 32, 62 may be calculated based, for example, on a mathematical model of the catheter. For instance, the magnetic sensor responses/positions may be used with a catheter model to generate a shape of the catheter. The catheter shape generated from the positions of the magnetic sensors may then be utilized to predict or calculate positions of the electrodes (e.g., actual positions) based on the known orientation between the electrodes and magnetic sensors for the generated catheter shape. For example, such a mathematical model of the catheter may utilize specifications associated with the catheter. Such specifications may define the position of the electrodes with respect to the magnetic sensors (e.g., distance between a magnetic sensor and adjacent electrode). Further, such a catheter model may utilize the position of the magnetic sensors in a three-dimensional space to determine an accurate deflection of the catheter. This information, in addition to the spacing information, may be utilized to determine (e.g., calculate) the actual positions of each electrode in a three-dimensional space. Stated otherwise, a catheter shape generated from the electrode responses may be compared with a catheter shape generated from the magnetic responses to determine differences in electrode positions.

As previously noted, such a catheter model refers to a catheter 12' or 12" for which a set of parameters (e.g., position, orientation, shape, length, number of electrodes 32, distance between adjacent electrodes 32, etc.) are defined such that actual positions (e.g., calculated positions) of the electrodes may be determined. Typically, such a mathematical model defines the catheter and the positions of the electrodes and/or magnetic sensors in a coordinate system associated with the catheter 12. By way of example, for a curved or linear one-dimensional catheter 12 (e.g., see FIG. 2), $U_i$ may represent a coordinate in the catheter coordinate system for an electrode i. This value $U_i$ may be a scalar value representing an arclength between the distal-most electrode (e.g., electrode 32A) and electrode i along shaft 26 of catheter 12. A curve parameter may represent the curvature of the catheter. The parametric form (e.g., catheter model) of the catheter 12 can be then described which defines the possible domain in which the actual position of the electrodes 32 lie. For curved or linear one-dimensional catheters, the true positions are described by a single curve of constant curvature, such that the true position of each electrode must fit a curve defined by the curve parameter. For the exemplary mapping or planar catheter 12' (see e.g., FIG. 4A), $U_i$ may be a two-dimensional coordinate in plane defined by a surface of the catheter 12'. A first term $(U_i,1)$ specifies a distance in the distal to proximal direction $U_i$ along central axis of catheter 12', and a second term $(U_i,2)$ specifies a distance from central axis perpendicular to the central axis, for example, direction $U_2$. In addition, the curvature is composed of a curvature term and torsion term. The curvature κ and torsion τ may be constant over the plane defined by the surface of the catheter 12'. For two-dimensional catheters, the true positions are described by an exemplary two-dimensional parametric form including curvature (κ) and torsion (τ) terms. Models for both the linear catheter 12 (e.g., FIG. 2) and the illustrated planar catheter 12' or 12" are set forth in U.S. Pat. Pub. No. 20180014751, as incorporated above.

The difference between the measured positions and the actual positions of the individual electrodes may be described as deviations 70 from their actual positions (e.g., calculated positions), as determined by the magnetic sensors and/or the catheter model. Each deviation 70 may represent three-dimensional information (e.g., vector) that maps the measured position to its actual position. Though illustrated as identifying the deviations 70 between the measured and the actual positions of the electrodes while the paddle 50 of the mapping catheter 12" is in a planar configuration, it will be appreciated that similar measurements may be obtained for multiple configurations (orientations and deflections) of the mapping catheter where the paddle 50 is bent, curled buckled or otherwise deflected from its planar form. In any orientation and/or deflection, the measured positions and actual positions of the electrodes may be determined based on the positions of the magnetic sensors. This process may be repeated for hundreds or thousands of mapping catheter orientations and/or deflections, for instance in a lab setting. For each orientation and/or deflection, a 'map' may be generated between the measured electrode positions and the actual electrode positions. A database of such maps may subsequently be used to map measured electrode positions to their actual positions. That is, such a database may be utilized to correct raw electrode positions obtained from a standard catheter (e.g., planar catheter 12' of FIG. 4A that does not include magnetic sensors on it paddle) to a more accurate positions.

While theoretically possible to generate a map database directly correlating measured positions to actual positions for use in correcting raw electrode positions (e.g., from a clinical usage catheter) to actual positions, the multitude of possible orientations and/or deflections of a catheter may make such a map database infeasible or otherwise impracticable. That is, a given set of measured electrode positions in a three-dimensional space (e.g., patient body) may not directly correspond to a known mapping between measured and actual positions. Accordingly, the present disclosure is directed to utilizing measured and actual positions obtained from a mapping catheter to train a machine learning algorithm. Once trained, such a machine learning algorithm may take any set of measured electrode positions from a clinical usage catheter and map those positions to actual positions. Stated otherwise, the machine learning algorithm may infer or predict the actual electrode positions of any set of measured electrode positions based on the training of the algorithm. While potentially not representing an absolute or true location of the electrode, the inferred or calculated positions (e.g., actual positions) will have an accuracy that is greater than the measured positions alone.

Embodiments of the present disclosure employ machine-learning algorithms to learn complex mapping between input parameters (e.g., raw electrode measurements/positions) and the output parameters of interest (e.g., actual electrode measurements/positions). The machine-learning algorithms do not rely on an a priori assumed model describing the relationship between the inputs and the outputs. Rather, the machine learning algorithms determine an optimal mapping between the input parameters and the output parameters via a statistical approach to learn the mapping from training data.

In an embodiment, a machine-learning based method for modeling a mapping between input parameters and output parameters includes three phases: a training/learning phase, a validation phase, and a usage phase. The learning phase may be an offline process performed, for example, using lab data and/or lab generated data sets. In an embodiment, the learning phase uses sets of annotated training data (e.g., a database) with ground truth values (e.g., actual positions and/or deviations between measured and actual positions). In an embodiment, a database of measured electrode positions (e.g., electrode responses) with corresponding actual electrode positions (e.g., calculated from magnetic sensor positions and/or a catheter model) is generated. The database may further include magnetic sensor positions. Such a database may be generated from lab data collected with the mapping catheter as discussed above. In this database, each training set (e.g., ground truth values) may represented by a number of features, such as a three-dimensional location of each measured electrode position, the three-dimensional location of each actual electrode position (e.g., determined from the magnetic sensor positions) and/or the deviation (e.g., vector) therebetween. See, e.g., FIG. 5B. Further, each training set may include positions of the magnetic sensor(s). Further, the training sets may utilize raw electrode responses (e.g., impedance responses) and/or raw magnetic measurements rather than utilizing positional data (e.g., cartesian, polar, spherical etc.). No limitation of the training data should be inferred. The training phase then learns or trains a mapping between the features (e.g., measured positions) and the ground truth values by minimizing the best fit between the features and ground truth values over the entire training database. Of note, such a database may include thousands or tens of thousands of training sets. At this time, a mathematical model is initialized to predict actual electrode locations based on an input of raw or measured electrode locations.

Once the initial learning phase is completed, the initialized mathematical model is verified to further refine the mathematical model. In one embodiment, additional data may be collected during, for example, animal testing utilizing the mapping catheter. In such an embodiment, raw/measured electrode positions received from the electrodes of the mapping catheter (e.g., which may be disposed in-vivo) may be applied to the mathematical model to predict or calculate the actual positions of the electrodes. The calculated positions (e.g., actual positions) of the electrodes may then be utilized to predict the shape of the catheter. That is, the calculated positions may be utilized as data points in a catheter model to generate an image of the catheter in a three-dimensional space. The magnetic sensor positions received from the mapping catheter may then be used to minimize the error in the mathematical model. By way of example, upon predicting a shape of the catheter, a predicted location or position of each magnetic sensor on the predicted shape may be generated. These predicted positions may be compared with the actual measured positions of the corresponding magnetic sensors to determine an error in the mathematical model. Such error may be utilized to further update and refine the mathematical model to define a correction model operable for clinical use.

The usage phase is an operation process utilized for patients during a procedure. In application, a set of raw/measured electrode positions are acquired by a clinical usage catheter (e.g., catheter 12' FIG. 4A) corresponding in shape and construction to the mapping catheter (e.g., catheter 12" FIG. 4B) utilized to generate the correction. The measured electrode locations are input to the trained and refined mathematical model (i.e., the correction model). The correction model outputs actual locations of the electrodes, which are utilized by the model construction system to generate an image of the clinical usage catheter.

The type of machine learning algorithm used to train the mapping may be, among others, a supervised, semi-supervised, transductive, or reinforcement based learning algorithm. For example, machine learning algorithms, such as regression algorithms (linear, non-linear, or logistic), decision trees or graphs, association rule learning, artificial neural networks, support vector machines, inductive logic programming, Bayesian networks, instance-based learning, manifold learning, sub-space learning, deep learning, dictionary learning, etc., may be used. The following discussion utilizes a deep learning neural network. However, it will be appreciated that the present disclosure is not limited to a deep learning neural network and that other machine learning algorithms may be implanted with the described systems and methods.

Figure 6:
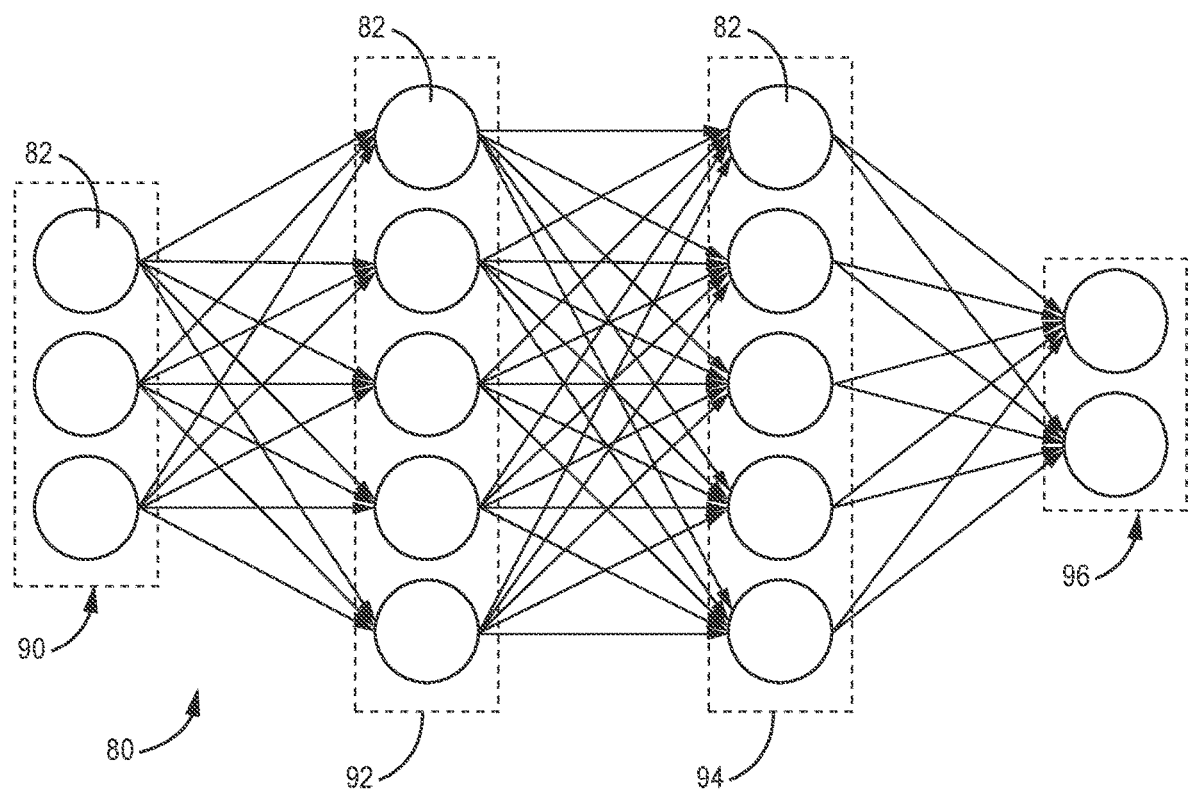
FIG. 6 illustrates one embodiment of a machine learning algorithm.

FIG. 6 illustrates an embodiment of a feed forward neural network 80. In this embodiment, the neural network 80 forms a mathematical model (e.g., correction model). The neural network 80 consist of a large number of computing units called neurons or nodes 82 each having multiple inputs and a single output (which may be output to multiple forward nodes). The nodes are typically connected in a layers '1' (e.g., layers 90-96) with the output of nodes in one layer being connected to all nodes in a forward layer. Deep learning represents a neural network with at least two hidden layers (e.g., layers 92, 94 between the input layer 90 and the output layer 96). Deep learning describes learning that includes learning hierarchical features from raw input data input into the input layer 90 to make predictions at the output layer 96. Deep learning models include deep neural networks (DNN), convolutional deep neural networks, deep belief networks, etc. In any arrangement, DNNs have multiple layers that enable hierarchical feature learning, as described above.

Broadly, the neural network 80 is designed to recognize features or patterns by mapping inputs to outputs by finding correlations between the inputs and outputs. Each node combines input data with a set of coefficients, or weights (e.g., connections between the nodes), that either amplify or dampen that input assigning significance to the input(s) for the task the algorithm is learning. The input-weight products are summed and passed through an activation function to generate an output that forms the next layer's input. Generally, each cycle of the neural network involves an estimation (e.g., output), an error measurement and an update in the weights and/or coefficients. In an embodiment, the error may be calculated based on a difference between an estimation and ground truth values. The neural network measures the error and attempts to adjust the weights to the extent that they contributed to the error. The process repeats in an effort to minimize the error.

In an embodiment, an output of a node i in a layer, called the activation, is computed as a function of its inputs as follows:

$$a_i(l)=F((\Sigma_{j=1\ldots k}w_{i,j}(l-1,l)*a_j(l-1))+b_i)$$

where $w_{ij}$ is the weight associated with the connection between nodes i and j and $b_i$ is a bias term associated with node i. The weights and bias terms constitute the parameters of the network to be learned to accomplish the specified task.

The activation function, F, associated with individual nodes in the network is a pre-defined non-linear function. In some embodiments, the activation function includes a sigmoid or hyperbolic tangent.

In an embodiment, the neural network 80 may be trained by back-propagation using gradient descent (e.g., to minimize error). Stochastic gradient descent is a variant that may be used where training inputs are processed in a random order. The inputs may be processed one at a time with the following steps performed for each input to update the model weights.

Activation describes the output of each node i in a given layer. The activation a may be computed by a process called feed-forward evaluation. The activation a may be computed as a function of k inputs from nodes j in a preceding layer (e.g., l–1), though the first layer utilizes input data. If $w_{ij}(l-1,l)$ is the weight associated with a connection between node j in layer l–1 and node i in layer l, then the feed-forward evaluation is as follows:

$$a_i(l)=F((\Sigma_{j=1\ldots k}w_{i,j}(l-1,l)*a_j(l-1))+b_i),$$

where b is a bias term for the node i. Error terms, δ, are computed for each node i in the output layer $l_n$, first as follows:

$$\delta_i(l_n)=(t_i(l_n)-a_i(l_n))*F'(a_i(l_n)),$$

where t(x) is the true value of the output and F'(x) is the derivative of F(x). These error terms may then be back-propagated for each node i in layer l connected to nodes m in layer l+1 as follows:

$$\delta_i(l)=(\Sigma_{j=1\ldots m}\delta_j(l+1)*w_{ji}(l,l+1))\cdot *F'(a_i(l)).$$

The error terms are used to update the weights (and biases similarly) as follows:

$$\Delta w_{ij}(l-1,l)=\alpha*\delta_i(l)*a_j(l-1) \text{ for } j=1\ldots k,$$

where α is a learning rate parameter.

This process may be repeated for each input until an entire training dataset has been processed, which constitutes a training cycle or epoch. At the end of a training cycle, the model prediction error may be computed on a validation set. Typically, training continues for multiple cycles, reprocessing the training data set each time, until the validation set error converges to a desired value below a predetermined threshold. The trained model may then be evaluated on test data.

Figure 7:
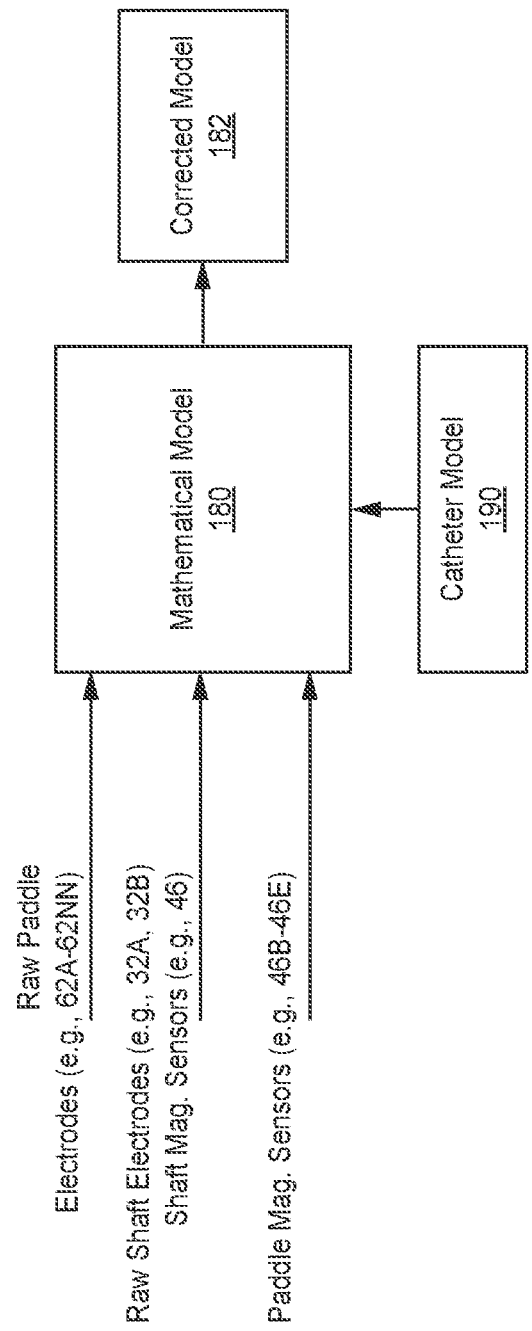
FIG. 7 illustrates the initial training of a machine learning algorithm.

FIG. 7 illustrates an embodiment of a training or learning phase for a mathematical model 180 (e.g., machine learning algorithm, feed forward neural network 80, etc.). In the illustrated embodiment, the mathematical model receives information (e.g., input values) from the mapping catheter 12" illustrated in FIG. 4B. However, it will be appreciated that, when utilized with differently configured catheters, such a mathematical model may be trained with different input values corresponding to such a catheter. In the illustrated embodiment, the mathematical model 180 receives information corresponding to the raw paddle electrode responses or positions acquired from the paddle electrodes 62A-62NN of the mapping catheter 12". The mathematical model 180 also receives inputs from the shaft electrodes 32A, 32B, the shaft magnetic sensor 46A and the magnetic sensors 46B-46E disposed on the paddle of the mapping catheter 12".

Though illustrated as a single set of inputs, it will be appreciated that during learning phase thousands or even tens of thousands of input sets may be input to the mathematical model 180. In an embodiment, each input set of data may be annotated to identify the deviation between the measured positions of the electrodes and their actual positions based on the magnetic sensors. See, e.g., FIG. 5B. In such an embodiment, the mathematical model 180 may be trained on labeled data in a supervised learning process. The model minimizes the error (e.g., adjusts the model) between predicted electrode positions and the actual electrode positions that are known from the labeled training sets. However, it will be appreciated that such labeled data is not necessary to train the mathematical model 180. That is, the mathematical model 180 may be trained on unlabeled data in an unsupervised learning process. Further, a catheter model 190 may be utilized to constrain the mathematical model 180 such that the mapping generated by the mathematical model is within realistic bounds as determined by the physical construction of the catheter. In any arrangement, upon completing the training on the training data sets (e.g., hundreds, thousands or tens of thousands of data sets), a corrected model data set 182 (e.g., initially trained mathematical model) may be generated identifying an initial mapping between the measured electrode positions and the actual electrode positions.

Figure 8:
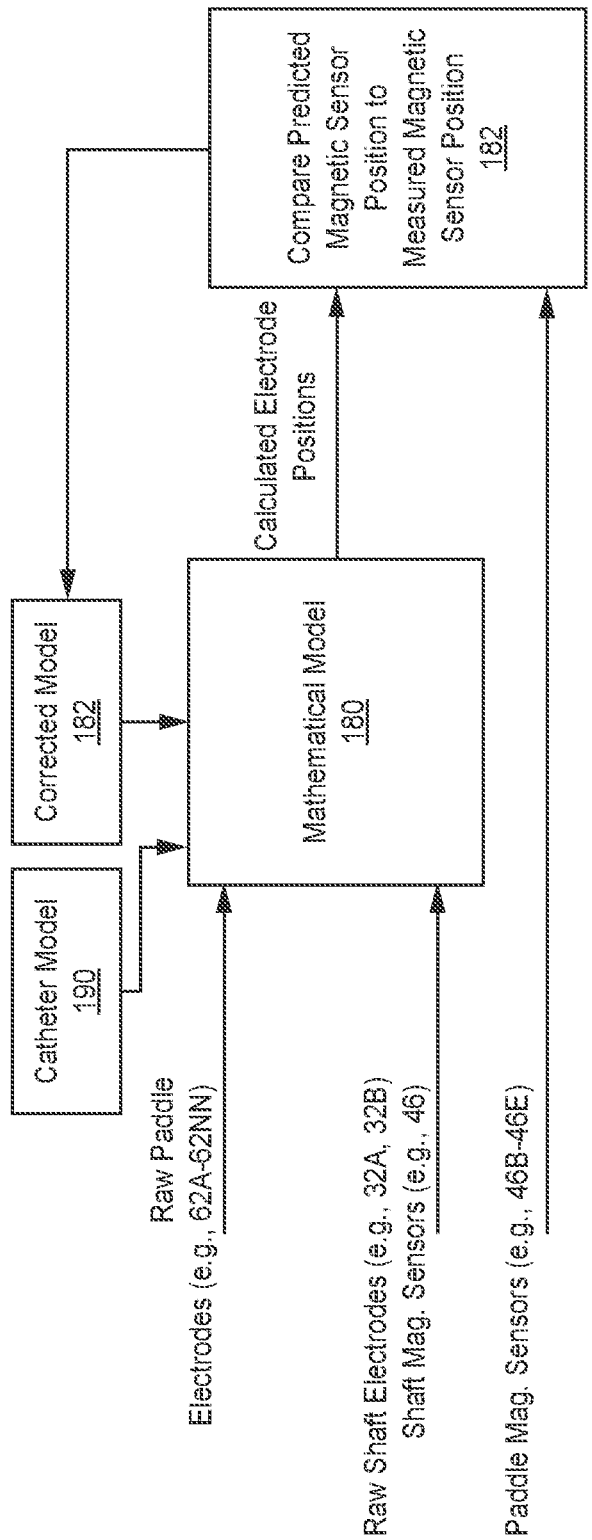
FIG. 8 illustrates verification training for the machine learning algorithm of FIG. 7.
Figure 9:
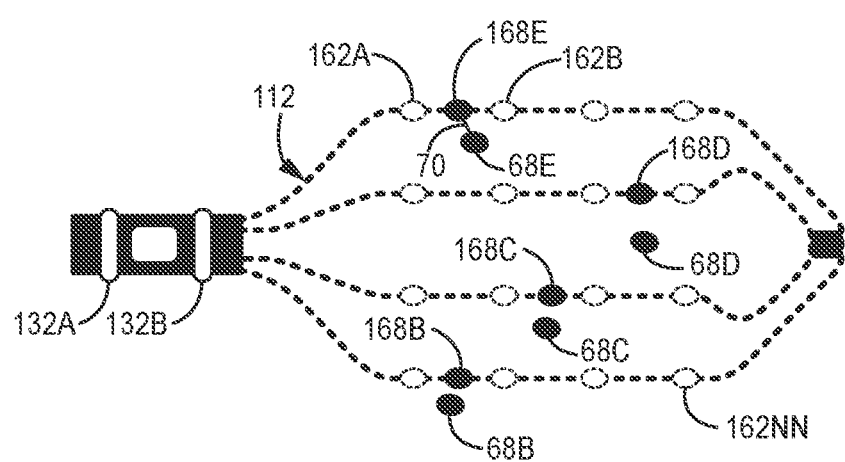
FIG. 9 illustrates shape prediction of a medical device and comparing predicted sensor positions to measured sensor positions.

FIG. 8 illustrates a validation phase for refining the initially trained mathematical model 180 (e.g., previously the corrected model data set). As shown, once initially trained using data from all electrodes and magnetic sensors of the mapping catheter 12" in the training phase, the inputs to the mathematical model in the validation phase is limited to the paddle electrodes 62A-62NN, the shaft electrodes 32A-B, and shaft magnetic sensor 46A (if present). See FIG. 4B. Data points (e.g., positions) from the paddle magnetic sensors 46B-E of the mapping catheter 12" are only utilized to adjust the mathematical model 180 and are no longer input into the mathematical model 180. The omission of the paddle magnetic sensor data from the mathematical model results in a model that will correspond to the clinical usage catheter 12', which will be utilized in actual medical applications (See. e.g., FIG. 4A) and which lacks magnetic sensors on its paddle. Referring to FIG. 4B, the initially trained mathematical model 180 of the present embodiment predicts the positions of the paddle electrodes 62A-62NN and shaft electrodes 32A, 32B. This is illustrated in FIG. 9 where sixteen predicted paddle electrode positions 162A-162NN and two shaft electrode positions 132A, 132B are shown. These positions or data points may be utilized with a catheter model 190 to generate a predicted shape 112 of the catheter as illustrated by the dashed lines in FIG. 9. Based on the predicted shape 112 of the catheter, the predicted positions 168A-D of the magnetic sensors on the paddle and/or shaft (not shown) may likewise be generated. For instance, a predicted position (e.g., position 168E) of a magnetic sensor based may be known to be halfway (e.g., potentially on a curve based on the catheter model) between two adjacent predicted electrode positions 162A and 162B. The difference or deviation 70 between the predicted position 168A of the magnetic sensor and the measured position 68E of that magnetic sensor (e.g., error) may be utilized to further adjust the mathematic model resulting in a corrected model data set 182. The corrected model data set 182 may then become the mathematical model 180 for the next cycle. The process may repeat to further minimize the error until the error is below a predetermined threshold.

In an embodiment, the validation phase occurs during in-vivo data collection using the mapping catheter 12". In an embodiment, the mapping catheter 12" collects data during animal testing and the validation or refinement of the mathematical model occurs simultaneously. Such in-vivo data collection using the mapping catheter 12" allows for the collection of thousands, hundreds of thousands and/or millions of inputs for use in training and refining the mathematical model. In an embodiment, the mapping catheter 12" is inserted into a three-dimensional space heart (e.g., heart chamber) and swept around the space while collecting and correlating data from the magnetic sensors and the electrodes. The data collection is done for multiple orientations and deflections. At the end of the data collection and validation phase, the mathematical model 182 will typically converge below a predetermined error threshold defining a correction model for use during medical procedures.

Figure 10:
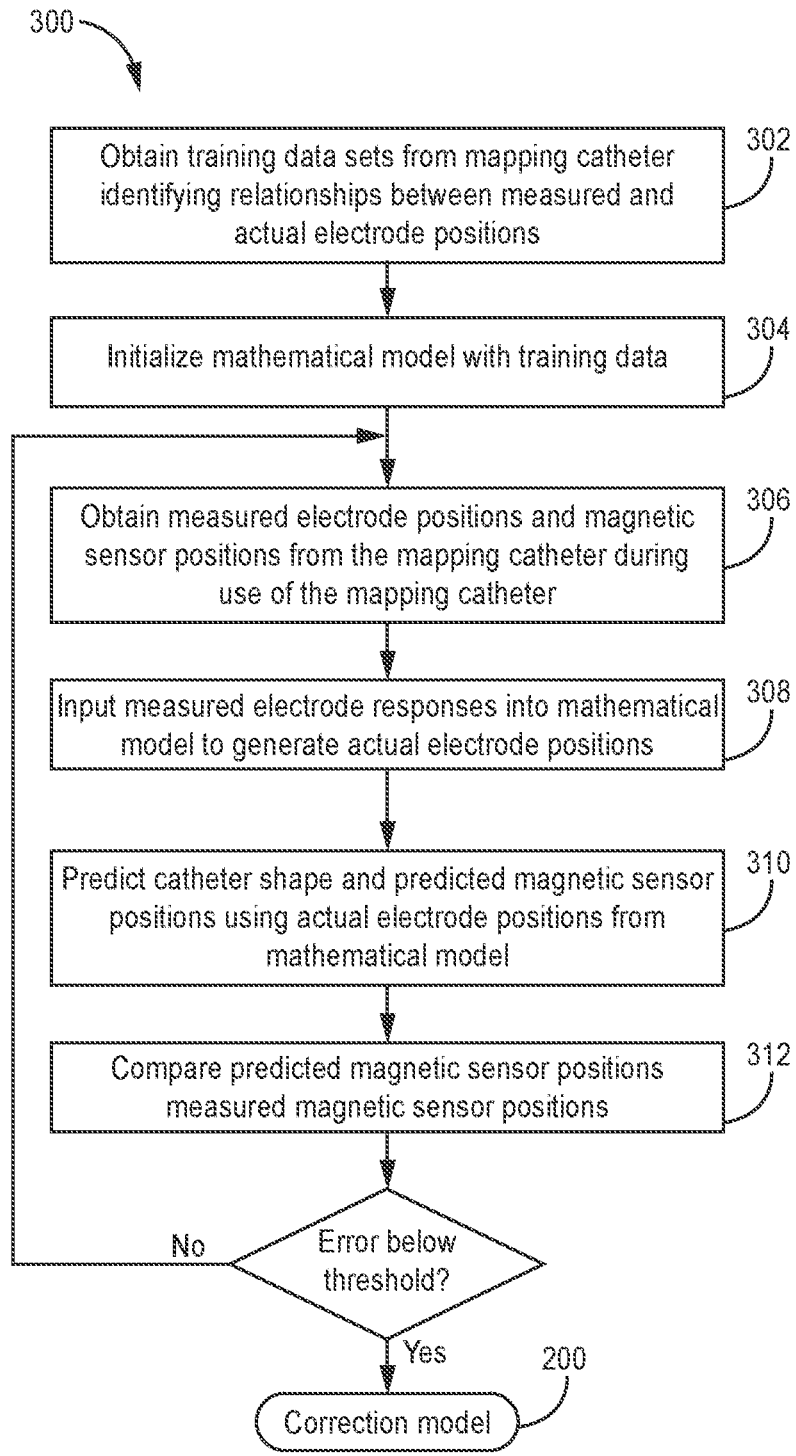
FIG. 10 illustrates a process flow sheet of the initialization and verification of a machine learning algorithm.

FIG. 10 illustrates a process flow sheet of the overall process 300 of the initial learning phase and the validation phase. Initially, training data set 302 are obtained (e.g., from the mapping catheter) that have known relationships between measured and actual electrode positions. The training data sets are input into a mathematical model (e.g., deep neural network) to initialize 304 the model. Once initialized, data may be obtained 306 from the mapping catheter while in use (e.g., during animal testing). The measured electrode positions from the mapping catheter may be input into to the mathematical model to generate 308 a set of predicted electrode positions. These predicted positions (e.g., calculated positions) are used to predict a catheter shape (e.g., inputting actual positions into a catheter model) and predict 310 magnetic sensor positions. The predicted magnetic sensor positions are compared 312 to measured magnetic sensor positions to determine error for the model. If the error exceed a predetermined threshold, it may be back-propagated through the model and the process may continue. After a predetermined number of cycles and/or once an error is below a predetermined threshold, the mathematical model may converge. That is, the mathematical model may predict actual electrode positions with an accuracy for use in medical applications thereby defining a correction model 200.

FIGS. 11 and 12A-12C illustrate the operational or usage phase of the correction model 200. In the illustrated embodiment, the correction model 200 receives inputs from the clinical usage catheter 12' of FIG. 4A. The clinical usage catheter 12' is configured for use in medical procedures and is free of magnetic sensors on its paddle 50 though otherwise configured substantially identically to the mapping catheter 12" utilized to generate the correction model. Measured raw electrode responses/positions 64A-NN from the sixteen paddle electrodes 62A-NN, raw responses from shaft electrodes 32A, 32B and the magnetic response/position from the magnetic shaft sensor 46A form inputs to the correction model 200. This is illustrated in FIG. 12A. The correction model 200 maps these responses from their measured positions to their adjusted or actual positions 66. See FIG. 12B. The actual positions are then utilized with the catheter model (e.g., model construction system 14) to render a shape 112 of the catheter 12', which may be output as an image to a display. See FIG. 12C.

It should be understood that system 10, model construction system 14, and processing apparatus 16, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for correcting electrode positions of medical devices configured for disposition within a patient body, the method comprising:
    acquiring, from a testing catheter having a plurality of electrodes and a plurality of magnetic sensors, a plurality of data sets, each data set including measured positions of the electrodes and measured positions of the magnetic sensors;
    mapping, for each data set, a measured position of each electrode to a calculated electrode position that is determined, at least in part, from the measured positions of the magnetic sensors to generate a correction model, wherein the correction model maps measured electrode positions to calculated electrode positions within a single reference frame;
    acquiring a subsequent set of measured electrode positions for a set of electrodes included as part of a clinical usage catheter, wherein the set of electrodes have an equal number and common configuration as the plurality of electrodes of the testing catheter;
    inputting the subsequent set of measured electrode positions into the correction model to generate a set of calculated electrode positions, wherein the measured electrode positions and the calculated electrode positions are located within a single reference frame;
    generating a catheter shape of the clinical usage catheter based on the set of calculated electrode positions; and
    displaying an image of the catheter shape.

2. The method of claim 1, wherein mapping further comprises:
    using a catheter model corresponding to the catheter to generate a catheter shape of the catheter based on the measured positions of the magnetic sensors; and
    generating, for each of the plurality of electrodes, the calculated electrode position from the catheter shape.

3. The method of claim 1, wherein mapping comprises:
    training a machine-learning algorithm using the plurality of data sets, wherein the machine-learning algorithm defines the correction model.

4. The method of claim 3, wherein training the machine-learning algorithm comprises training a Deep Neural Network (DNN).

5. The method of claim 3, wherein the measured positions of the electrodes and the measured positions of the magnetic sensors from the plurality of data sets are inputs to the machine-learning algorithm and the machine-learning algorithm maps the inputs to calculated electrode positions.

6. The method of claim 3, wherein the inputting of the subsequent set of measured electrode positions into the correction model comprises:
    inputting the subsequent set of measured electrode positions into the machine learning algorithm, wherein the machine-learning algorithm outputs the set of calculated electrode positions.

7. The method of claim 1, wherein the acquiring of the plurality of date sets comprises:
    acquiring data sets for multiple positions and orientations of the catheter while disposed in a three-dimensional space.

8. A system for correcting electrode positions of medical devices configured for disposition within a patient body, the system comprising:
    a medical positioning system configured to measure responses of electrodes and magnetic sensors in a three-dimensional space;
    a processor and memory for storing non-transitory computer readable instructions to:
        access a correction model trained with a plurality of sets of measured electrode positions and measured magnetic sensor positions acquired from a testing catheter having a plurality of electrodes and a plurality of magnetic sensors, wherein the measured electrode positions and the measured magnetic positions are input into the correction model to map the measured electrode positions to calculated electrode positions determined from the measured magnetic sensor positions, wherein the measured electrode positions and calculated electrode positions are located in a single reference frame;

acquire a set of measured electrode positions of a clinical usage catheter from the medical positioning system, wherein the clinical usage catheter has a common shape and electrode configuration as the testing catheter;

input the set of measured electrode positions into the correction model to generate a set of calculated electrode positions, wherein the measured electrode positions and the calculated electrodes positions are within a single reference frame; and input the calculated electrode positions into a catheter model corresponding to the clinical usage catheter to generate a catheter shape based on the set of calculated electrode positions; and a display configured to display an image of the catheter shape.

9. The system of claim 8, wherein the non-transitory computer-readable instructions comprising instructions to perform the step of accessing the correction model further comprises instructions to:

access a plurality of sets of measured responses acquired from the testing catheter having the plurality of electrodes and the plurality of magnetic sensors; and map, for each set of measured responses, a measured position of each electrode to a calculated electrode position determined from the magnetic sensor positions to generate the correction model.

10. The system of claim 9, wherein the non-transitory computer-readable instructions further comprise instructions to:

input, for each set of measured responses, measured positions of the plurality of magnetic sensors into a catheter model corresponding to the testing catheter to generate a catheter shape of the testing catheter; and generate, for each of the plurality of electrodes, the calculated electrode position from the catheter shape.

11. The system of claim 9, wherein the non-transitory computer-readable instructions further comprise instructions to:

utilize the plurality of sets of measured responses to train a machine-learning algorithm, wherein the machine-learning algorithm defines the correction model.

12. A non-transitory computer-readable medium storing instructions for training and using a machine-learning algorithm to correct electrode positions, executable to:

initially train a machine-learning algorithm with a first plurality of sets of measured electrode positions and measured magnetic sensor positions acquired from a testing catheter having a plurality of electrodes and a plurality of magnetic sensors, wherein the measured electrode positions and the measured magnetic positions are input into the machine-learning algorithm to map the measured electrode positions to calculated electrode positions determined from the measured magnetic sensor positions, wherein the measured electrode positions and calculated electrode positions are located in a single reference frame;

input a subsequent set measured electrode positions acquired from the testing catheter into the machine-learning algorithm to generate a set of calculated electrode positions;

generate a catheter shape based on the set of calculated electrode positions utilizing a catheter model that corresponds to the testing catheter;

identify predicted magnetic sensor positions for one or more magnetic sensors of the catheter based on the catheter shape;

comparing the predicted magnetic sensor positions to a subsequent set of measured magnetic sensor positions corresponding to the subsequent set of measured electrode positions to calculate an error value for the machine-learning algorithm; and refine the machine-learning algorithm using the error value.

13. The non-transitory computer-readable medium of claim 12, further comprising instructions to:

repeat the input, generate, identify and compare steps for additional subsequent sets of measured electrode positions and measured magnetic sensor for the catheter until a calculated error value is below a predetermined threshold, wherein the machine-learning algorithm defines a correction model.

14. The non-transitory computer-readable medium of claim 13, further comprising instructions to:

input a set of measured electrode positions into the correction model wherein the measured electrode positions are acquired from a clinical usage catheter with a set of electrodes corresponding in number and configuration to the plurality of electrodes of the testing catheter;

generate, from the correction model, a set calculated electrode positions for the electrodes of the usage catheter;

generate a catheter image of the usage catheter using the set of calculated electrode positions; and display the catheter image.

15. A method for correcting electrode positions of a medical device configured for disposition within a patient body, the method comprising:

acquiring a plurality of measured electrode positions from a clinical usage catheter configured for disposition in a patient body;

inputting the measured electrode positions into a trained machine-learning algorithm that maps measured electrode positions to calculated electrode positions within a single reference frame, wherein the machine learning algorithm is trained on training data obtained from a testing catheter having an identical electrode configuration as the clinical usage catheter and that further includes a plurality of magnetic sensors, wherein the machine-learning algorithm is trained based on the measured electrode positions and the measured magnetic positions provided by the testing catheter, wherein the measured electrode positions provided by the testing catheter are mapped to calculated electrode positions determined from the measured magnetic sensor positions provided by the testing catheter;

obtaining a set of calculated electrode positions from the machine-learning algorithm based on the inputted measured electrode positions received from the clinical usage catheter;

generating a catheter image of the clinical usage catheter using the set of calculated electrode positions; and displaying the catheter image.

16. A system for correcting electrode positions of a medical device configured for disposition within a patient body, the system comprising:

a medical positioning system configured to measure responses of electrodes and magnetic sensors in a three-dimensional space;

a processor and memory for storing non-transitory computer readable instructions to:
  acquire a plurality of measured electrode positions from a clinical usage catheter configured for disposition in a patient body;
  input the measured electrode positions into a trained machine-learning algorithm that maps measured electrode positions to calculated electrode positions within a single reference frame, wherein the machine learning algorithm is trained on training data obtained from a testing catheter having an identical electrode configuration as the clinical usage catheter and that further includes a plurality of magnetic sensors, wherein the machine-learning algorithm is trained based on measured electrode positions and measured magnetic positions provided by the testing catheter, wherein the measured electrode positions provided by the testing catheter are mapped to calculated electrode positions determined from the measured magnetic sensor positions provided by the testing catheter;
  obtain a set of calculated electrode positions from the machine-learning algorithm based on the inputted measured electrode positions received from the clinical usage catheter;
  generate a catheter image of the clinical usage catheter using the set of calculated electrode positions; and
a display configured to display the catheter image.

* * * * *